United States Patent
Warnick et al.

(10) Patent No.: US 8,157,845 B2
(45) Date of Patent: Apr. 17, 2012

(54) PIVOTABLE VETREBRAL SPACER

(75) Inventors: David R. Warnick, Spanish Fork, UT (US); Michael D. Ensign, Salt Lake City, UT (US)

(73) Assignee: Beacon Biomedical, LLC, Tequesta, FL (US)

( * ) Notice: Subject to any disclaimer, the term of this patent is extended or adjusted under 35 U.S.C. 154(b) by 603 days.

(21) Appl. No.: 11/856,483

(22) Filed: Sep. 17, 2007

(65) Prior Publication Data

US 2008/0009880 A1 Jan. 10, 2008

Related U.S. Application Data (63) Continuation-in-part of application No. 11/726,865, filed on Mar. 22, 2007, now Pat. No. 8,043,293.

(60) Provisional application No. 60/784,546, filed on Mar. 22, 2006, provisional application No. 60/845,488, filed on Sep. 18, 2006.

(51) Int. Cl.
 *A61B 17/88* (2006.01)
(52) U.S. Cl. .................. 606/279; 606/99; 606/86 A
(58) Field of Classification Search ............. 606/86 A, 606/99, 246–253; 623/17.11–17.16
See application file for complete search history.

(56) References Cited

U.S. PATENT DOCUMENTS

| | | | |
|---|---|---|---|
| 6,599,294 | B2 | 7/2003 | Fuss et al. |
| 6,696,073 | B2 | 2/2004 | Boyce et al. |
| 6,719,794 | B2 | 4/2004 | Gerber et al. |
| 6,942,697 | B2 | 9/2005 | Lange et al. |
| 6,974,480 | B2 | 12/2005 | Messerli et al. |
| 7,018,413 | B2 | 3/2006 | Kruger |
| 7,041,137 | B2 | 5/2006 | Fulton et al. |
| 2003/0139813 | A1 | 7/2003 | Messerli et al. |
| 2004/0097929 | A1 | 5/2004 | Branch et al. |
| 2006/0229627 | A1 * | 10/2006 | Hunt et al. ............ 606/86 |
| 2007/0213826 | A1 * | 9/2007 | Smith et al. ........... 623/17.11 |

* cited by examiner

*Primary Examiner* — Eduardo C Robert
*Assistant Examiner* — Christina Negrelli
(74) *Attorney, Agent, or Firm* — McHale & Slavin, P.A.

(57) ABSTRACT

According to one exemplary embodiment, a pivotable interbody spacer system includes an insertion instrument configured to manipulate a pivotable interbody spacer during surgical insertion, wherein the insertion instrument includes means for coupling the interbody spacer and a means for fixing the angular position of the interbody spacer. According to one exemplary method for inserting the interbody spacer in a spinal disc space, the interbody spacer is grasped by the insertion instrument and fixed at a first angular position; the interbody spacer is inserted into the surgical site; the interbody spacer is released from the first angular position; the insertion instrument is pivoted about the coupling such that the interbody spacer is in a second angular position; the angular position of interbody spacer is fixed in the second angular position; the insertion process continues until the interbody spacer is positioned in the desired location.

16 Claims, 10 Drawing Sheets

PIVOTABLE VETREBRAL SPACER

RELATED APPLICATIONS

This application is a continuation-in-part of U.S. patent application Ser. No. 11/726,865 filed Mar. 22, 2007 now U.S. Pat. No. 8,043,293 titled "Pivotable Interbody Spacer" which claims the benefit under 35 U.S.C. §119(e) of U.S. Provisional Patent Application No. 60/784,546 filed Mar. 22, 2006 titled "Pivotable Interbody Spacer." Additionally, the present application claims the benefit under 35 U.S.C. §119(e) of U.S. Provisional Patent Application No. 60/845,488 filed Sep. 18, 2006 titled "Pivotable Vetrebral Spacer". The afore mentioned applications are incorporated herein by reference in their entireties.

FIELD

The present system and method relate to bone fixation devices. More particularly, the present system relates to a spinal implant for interbody fusion to the spinal column.

BACKGROUND

The degeneration of the intervertebral disk, in particular, the degeneration of the nucleus pulposus, results in a loss of height in the affected disk space which is associated with a weakening of the annulus fibrosus and of the ligaments. As a consequence the spinal column becomes instable and is more susceptible to horizontal displacement of the vertebral bodies with respect to one another. This horizontal movement of vertebral bodies results in impairments of the nerve roots in this region and/or of the spinal marrow with pain resulting therefrom.

The principle treatment of these symptoms consists of the surgical removal of the nucleus pulposus and the insertion of support bodies in order to restore the normal height of the disk space.

There are a variety of demands on both the surgeon performing an intervertebral disk procedure and on the spinal spacers themselves.

A Transforaminal Lumbar Interbody Fusion (TLIF) is a surgical procedure that uses a posterior and lateral approach to access the disc space. To gain access to the disc space, typically a facet joint is removed and access is gained via the nerve foramen. While more technically demanding of the surgeon than other fusion techniques, a TLIF offers a number of clinical advantages. Specifically, when compared to a PosteroLateral Fusion (PLF), a TLIF approach leaves much more of the soft tissue intact, which is less traumatic for the patient. Further, a PLF does not provide access to the disc space.

While a PosteroLateral InterBody Fusion (PLIF) provides access to the disc space, a TLIF approach also provides access to the interbody space, but without the need for manipulation of neural elements, reducing the risk of post-operative neural deficit. Additionally, in a TLIF, only a single spacer is placed. More specifically the TLIF spacer is placed in the anterior aspect of the disc space, thus providing space for a substantial fusion mass in the posterior aspect of the disc space where the natural compression occurs.

However, traditional TLIF procedures do suffer from shortcomings. For example, to place the desired spacer in the anterior aspect of the disc space from an oblique posterior approach, traditional procedures demand that the spacer be released from the inserter and then tamped into place. The two step insertion of this spacer is generally recognized among surgeons as cumbersome.

SUMMARY

According to one exemplary embodiment, a pivotable interbody spacer includes a body defining an inner cavity and a plurality of teeth formed on one end of said spacer.

According to another exemplary embodiment, a pivotable interbody spacer system includes an spacer including a body defining an inner cavity and a plurality of teeth formed on one end of the spacer, and an insertion instrument associated with the spacer, wherein the insertion instrument includes a retractable latching mechanism and matching interior teeth configured to pivotably mate with said teeth formed on said spacer.

Furthermore, according to one exemplary embodiment, a method for pivotably implanting an interbody spacer includes coupling the spacer to a pivoting instrument, inserting the spacer through a nerve foramen, simultaneously pivoting and inserting the spacer until the spacer is inserted to its final position, and releasing the spacer from the instrument to facilitate removal of the instrument.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Fur-

DETAILED DESCRIPTION

The present specification describes a system and a method for pivotably inserting an interbody spacer, such as during a Transforaminal Lumbar Interbody Fusion (TLIF). According to one exemplary embodiment, a system including a pivotable interbody spacer and insertion instrument configured to pivotably manipulate the interbody spacer are provided herein. According to one exemplary embodiment, a plurality of teeth is formed on at least one end of the spacer and matching teeth are formed on an insertion instrument. According to one exemplary embodiment, the insertion instrument includes two opposing jaws configured to couple to an end of the pivotable interbody spacer. Further details of the present exemplary system and method will be provided below, with reference to the figures.

In the following description, certain specific details are set forth in order to provide a thorough understanding of various embodiments of the present system and a method for pivotably inserting an interbody spacer. However, one skilled in the relevant art will recognize that the present exemplary system and method may be practiced without one or more of these specific details, or with other methods, components, materials, etc. In other instances, well-known structures associated with interbody fusion have not been shown or described in detail to avoid unnecessarily obscuring descriptions of the present exemplary embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Figure 1A:
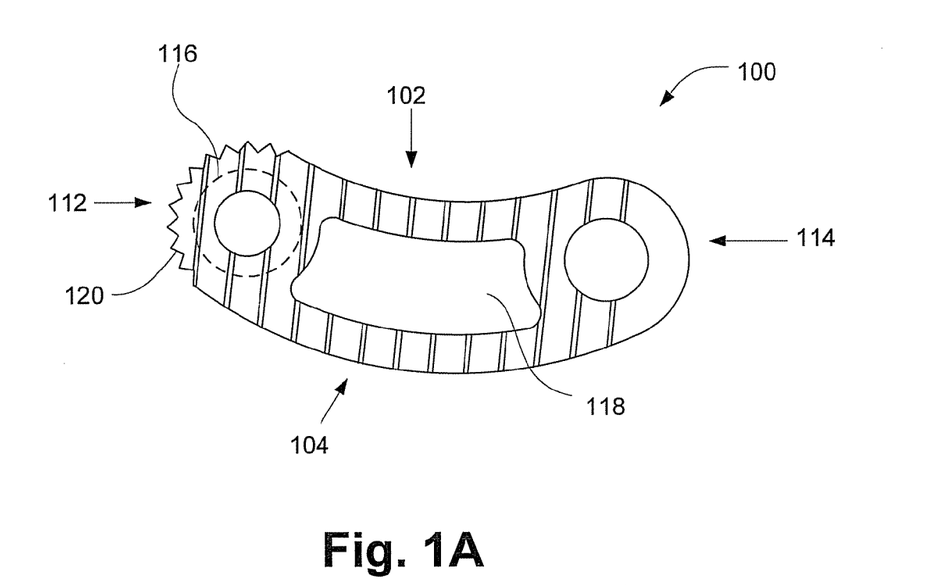
FIGS. 1A and 1B are a side view and a perspective view, respectively, of a pivotable interbody spacer, according to one exemplary embodiment.
Figure 1B:
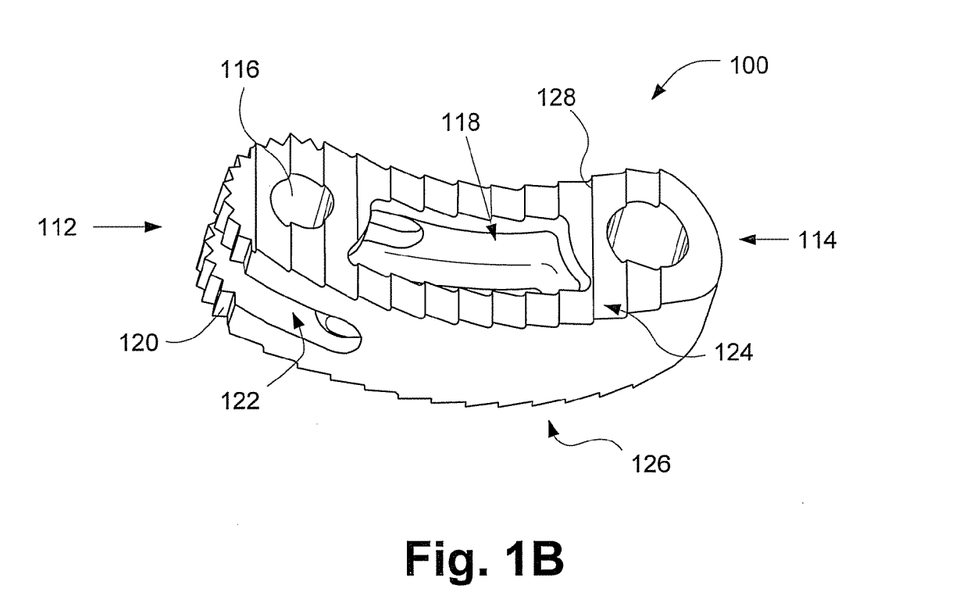

FIGS. 1A and 1B illustrate an interbody spacer (100), according to one exemplary embodiment. As illustrated in FIGS. 1A and 1B, the present exemplary interbody spacer (100) is designed for use as an intervertebral spacer in spinal fusion surgery, where portions of an affected disc are removed from between two adjacent vertebrae and replaced with an spacer that provides segmental stability and allows for bone to grow between the two vertebrae to bridge the gap created by disk removal.

As shown, the present exemplary interbody spacer (100) has an arcuate, "rocker-like" shape with concave anterior face (102) and a convex posterior face (104) to facilitate the insertion of the spacer through a narrow approach window into the disk space. As illustrated, the present interbody spacer (100) includes a proximal end (112) that will be closest to a surgeon during use, and a distal end (114) that will likely be the leading edge of insertion during use.

The central portion of the spacer body may have a variety of apertures and bores designed to facilitate and support bone growth. In one exemplary embodiment, the spacer (100) has a substantially hollow center (118). With the advent of bone morphogenic protein (BMP), the spacer is now seen as a potential delivery tool of the BMP. Consequently, many spacers are now hollow. However, the size of the internal cavity of the spacer is limited by the need to limit the size of the spacer and to maximize the surface area of the spacer. Too large of a spacer will not provide space for a fusion mass. Too small of a surface area will lead to subsidence of the spacer into the adjacent vertebral bodies. According to one embodiment, the spacer is hollowed out to increase cavity volume and surface area while minimizing overall size. Consequently, the present exemplary interbody spacer (100) employs geometry that provides for a small spacer with relatively large surface area and internal cavity (118). Other cavities and geometries may be included in the spacer structure, such as a hollow transverse cylinder (116).

According to one exemplary embodiment, the interbody spacer (100) has an upper face (124) and an opposing lower face (126). A series of ridges (128) traverse the upper and lower faces (124, 126). The ridges (128) are configured to facilitate the insertion of the interbody spacer (100) by preventing retrograde motion and slippage during the insertion process. After the surgery is complete, the ridges (128) also may provide increase surface area, encourage bone growth, and/or prevent dislocation of the interbody spacer (100).

Additionally, as illustrated in FIGS. 1A and 1B, the present interbody spacer (100) includes a plurality of teeth (120) or other frictionally engaging features on at least one end of the spacer (100). According to one exemplary embodiment, any number of protruding features, materials, or rough surface finishes disposed on at least one end of an interbody spacer (100) may be used to pivotably direct an interbody spacer (100) during surgical insertion. Particularly, according to one exemplary embodiment, the interbody spacer (100) has a plurality of teeth (120) disposed about the perimeter of the rounded proximal end (112). The teeth (120) allow for an insertion instrument to firmly grip the interbody spacer (100) and aid in the manipulation of the interbody spacer (100) during insertion. In one exemplary embodiment, the teeth (120), when coupled with an appropriate insertion instrument, may simplify a TLIF procedure by allowing the pivoting and tamping of the interbody spacer (100) without having to release it from the grasp of the insertion instrument.

As shown more particularly in FIG. 1B, the proximal end (112) of the interbody spacer (100) has an access gap (122) that allows access to internal features of the interbody spacer (100), such as the outer surface of the transverse cylinder (116) illustrated in FIGS. 1A and 1B. In alternative embodiments, the teeth (120) or other frictionally engaging features may be formed inside the access gap (122). For ease of explanation only, the present specification will describe the present system and method in the context of an spacer including external teeth (120) on at least one end thereof. In the illustrated embodiment, the distal end (114) of the interbody spacer (100) has a double elliptical leading edge for ease of insertion through the overlying tissues and into the intervertebral space.

Figures 2A, 2B:
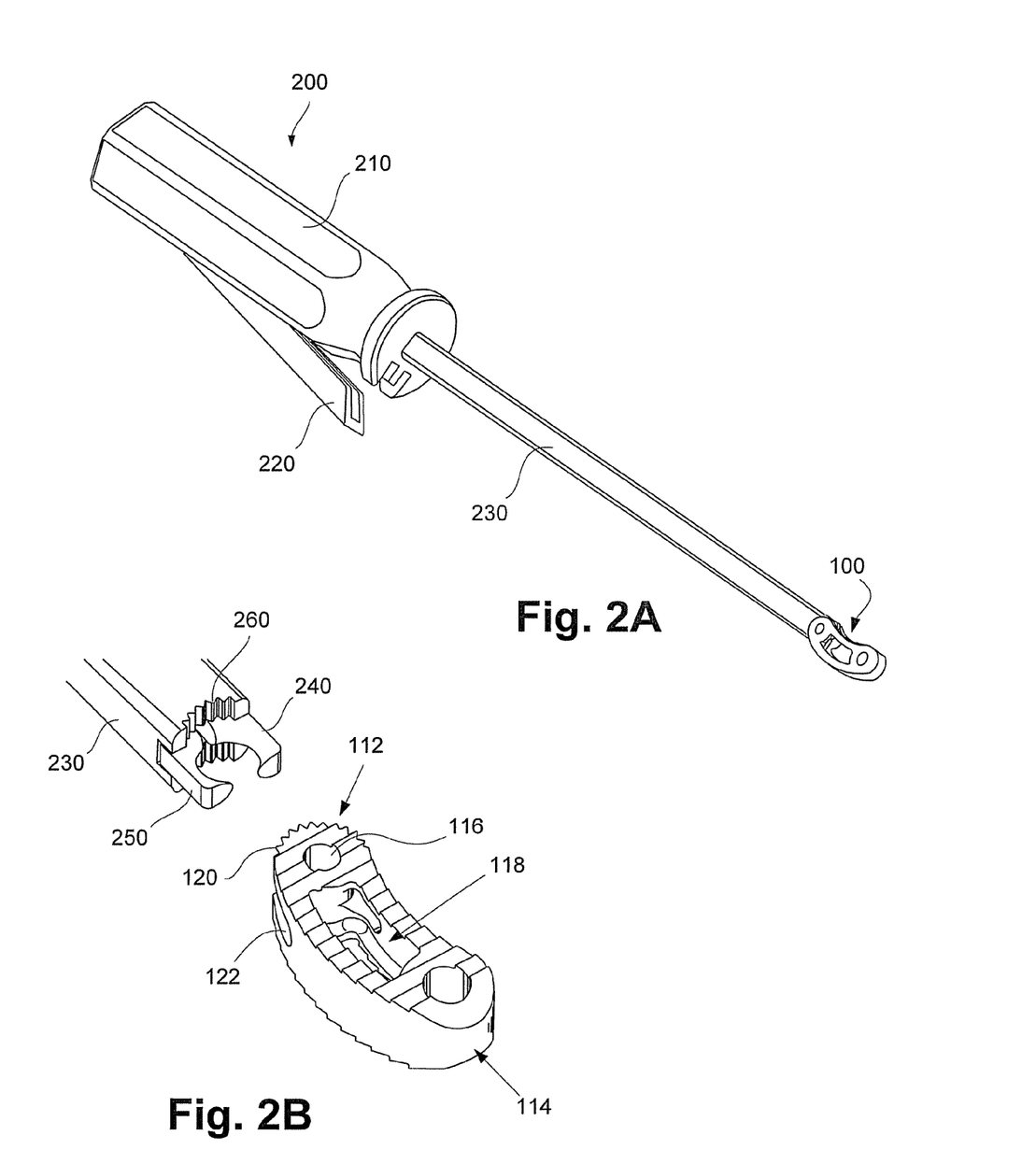
FIGS. 2A and 2B are perspective views of an insertion instrument configured to grasp and manipulate the pivotable interbody spacer of FIGS. 1A and 1B, according to one exemplary embodiment.

FIGS. 2A and 2B illustrate one exemplary insertion instrument (200) that may be used with the present pivotable interbody spacer (100). As illustrated in FIG. 2A, the insertion instrument (200) includes a handle (210) configured to facilitate manual grasping of the insertion instrument (200), a lever (220) pivotably connected to the handle (210), and a shaft (230) extending from one end of the handle (210). At a distal end of the shaft (230) a number of features are disposed which facilitate the grasping and subsequent manipulation of the pivotable interbody spacer (100), according to one exemplary embodiment.

As shown in FIG. 2B the shaft (230) terminates in a number of features configured to facilitate the grasping and subsequent manipulation of the interbody spacer (100) including opposing jaws or jaw members (240, 250) and frictional features designed to engage with the frictional features on the interbody spacer (100). In one exemplary embodiment the jaws can pass into the access gap (122) and around the outer perimeter of the transverse cylinder (116) to couple the interbody spacer (100) to the insertion tool (200). Additionally, the distal end of the shaft (230) has a concave surface with a plurality of teeth (260) that is configured to receive and engage the plurality of spacer teeth (120) disposed about the perimeter of the convex surface of the proximal end (112) of the interbody spacer (100).

Figure 3A:
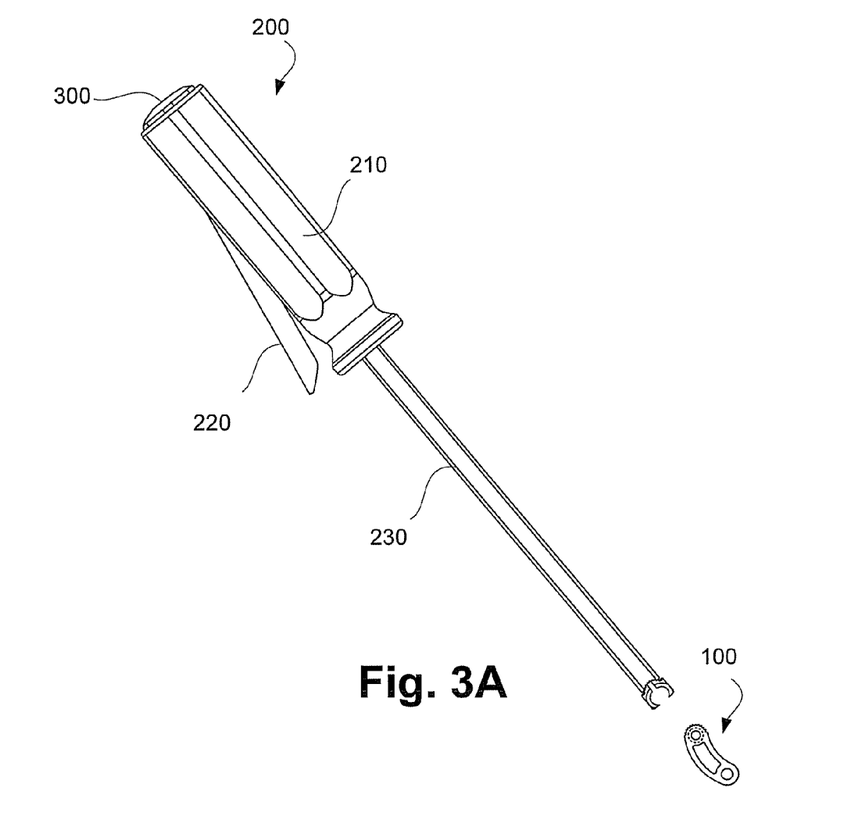
FIGS. 3A and 3B are side views of a pivotable interbody spacer and an insertion instrument, according to one exemplary embodiment.
Figure 3B:
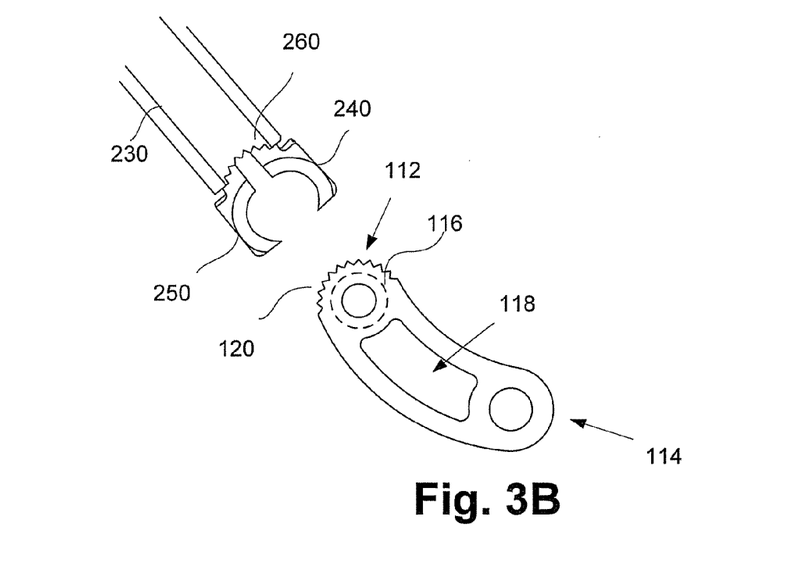

FIGS. 3A and 3B illustrate a side view of one exemplary embodiment of an interbody spacer (100) and an insertion instrument (200). The lever (220) is mechanically connected through interior mechanisms (not shown) to the opposing jaws or jaw members (240, 250) at the terminal end of the shaft (230). The lever (220) can be moved into three positions that correspond to three different jaw configurations. In FIG. 3A, the lever (220) is shown in a first position that corresponds to an open jaw configuration. As shown in FIG. 3B, in the open jaw configuration, the first jaw or jaw member (240) and the second jaw or jaw member (250) are extended out of the shaft body and apart from each other. In this open configuration, the jaws can pass into the access gap (122) and around the outer perimeter of the transverse cylinder (116). The spacing between the jaws or jaw members (240, 250) pass around the perimeter of the transverse cylinder (116) without substantial resistance, or such that the spacer "snaps" into the internal cylinder space created between the jaws (2340, 250).

Also shown in FIG. 3A is an impaction cap (300) on the end of the handle (210). The impaction cap (300) provides a durable and resilient surface for impacting the insertion instrument (200) to tamp the interbody spacer (100) into position.

Figures 4A, 4B:
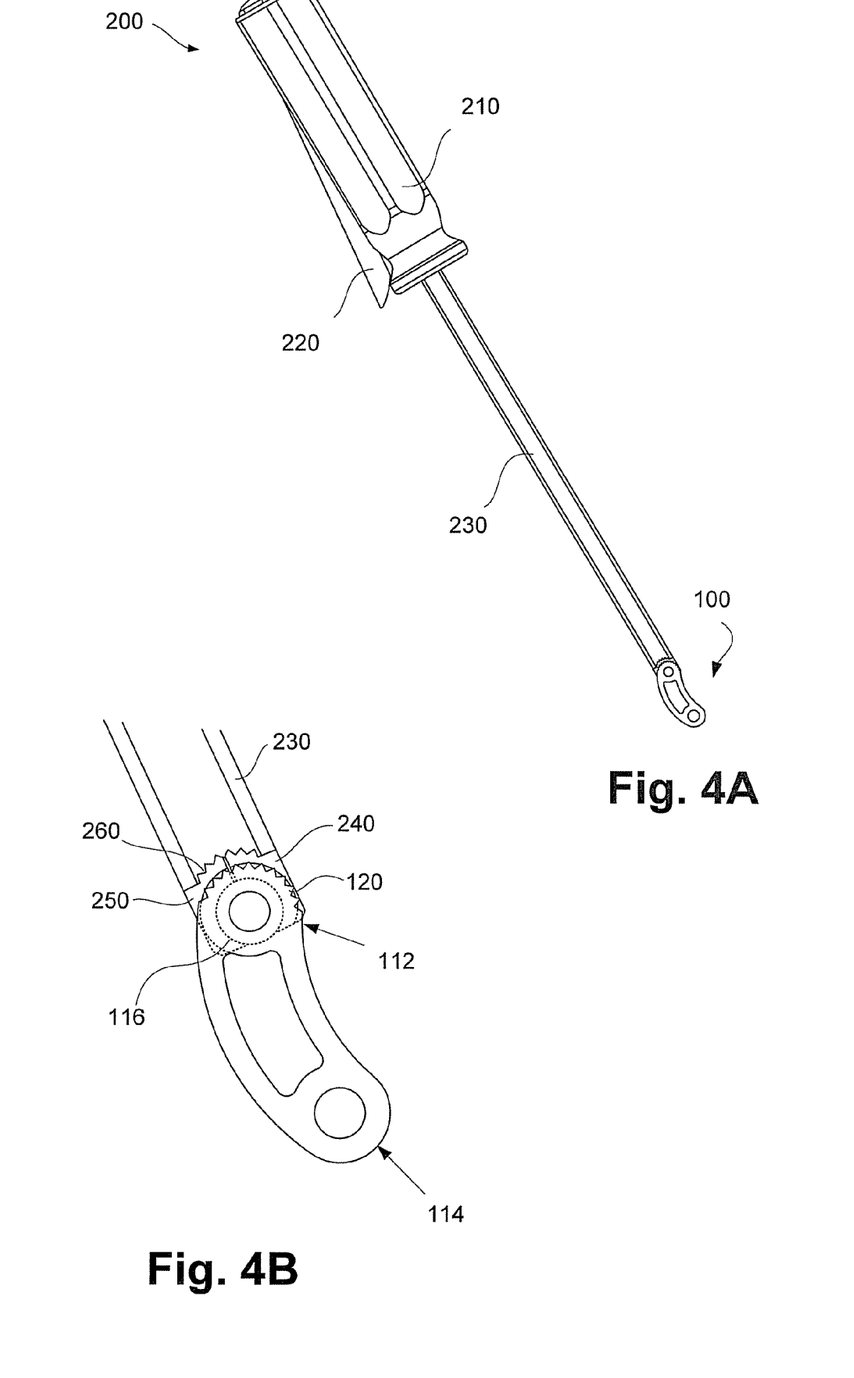
FIGS. 4A and 4B are side views of an insertion instrument rotatably grasping a pivotable interbody spacer, according to one exemplary embodiment.

FIGS. 4A and 4B illustrate side views of the insertion instrument (200) and the interbody spacer (100). FIG. 4A shows the lever (220) in a second position which corresponds to a closed jaw configuration. In the closed jaw configuration, the opposing jaws or jaw members (240, 250) are brought together around the outer perimeter of the transverse cylinder (116). The interbody spacer (100) is firmly grasped by the jaws or jaw members (240, 250) in a manner that still allows the outer perimeter of the transverse cylinder (116) to rotate within the internal space created by the closed jaws or jaw members (240, 250) without allowing the spacer (100) to be disengaged from the insertion instrument (200).

Figure 5A:
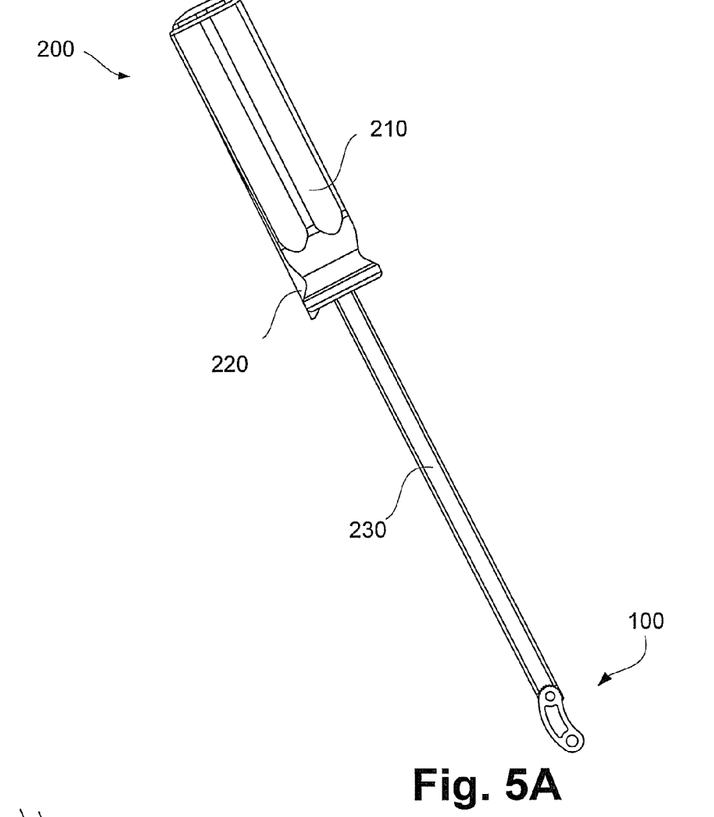
FIGS. 5A and 5B are side views of an insertion instrument fixably grasping a pivotable interbody spacer, according to one exemplary embodiment.
Figure 5B:
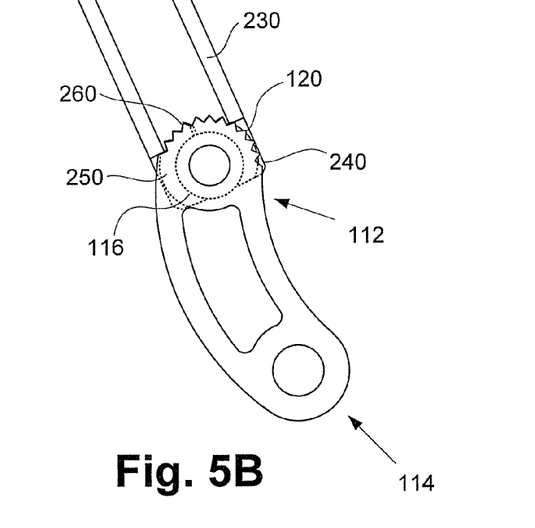

FIGS. 5A and 5B illustrate side views of the insertion instrument (200) and the interbody spacer (100). FIG. 5A shows the lever (220) in a third position which further restrains the spacer (100) by locking its rotation. This is particularly useful during impaction of the spacer (100) into position in the intervertebral space. In one exemplary embodiment the third lever position corresponds to a closed and retracted jaw configuration. In the closed and retracted jaw configuration the opposing jaws or jaw members (240, 250) are brought together around the outer perimeter of the transverse cylinder (116) and the jaws (240, 250) are retracted into the shaft (230) such that the frictional features on the shaft (260) engage the corresponding frictional features (120) on the spacer. The engagement of the frictional features prevents the pivoting of the spacer (100) with the jaws or jaw members (240, 250). For example, while the lever (220, FIG. 4A) is the second position, the spacer (100) can be pivoted into the desired angular position with respect to the insertion instrument (200). Then with the spacer (100) at the desired angle, the lever (220) is moved into a third position which retracts the jaws into the shaft, thereby engaging the shaft teeth (260) with spacer teeth (120). The interbody spacer (100) is firmly grasped by the jaws or jaw members (240, 250) and locked at the desired angle by the engagement of the mating teeth (120, 260). The spacer (100) can now be impacted into the disc space. The position and motion of the rigidly held spacer (100) can be precisely controlled by manipulating the insertion instrument (200).

Exemplary Method

Figure 6:
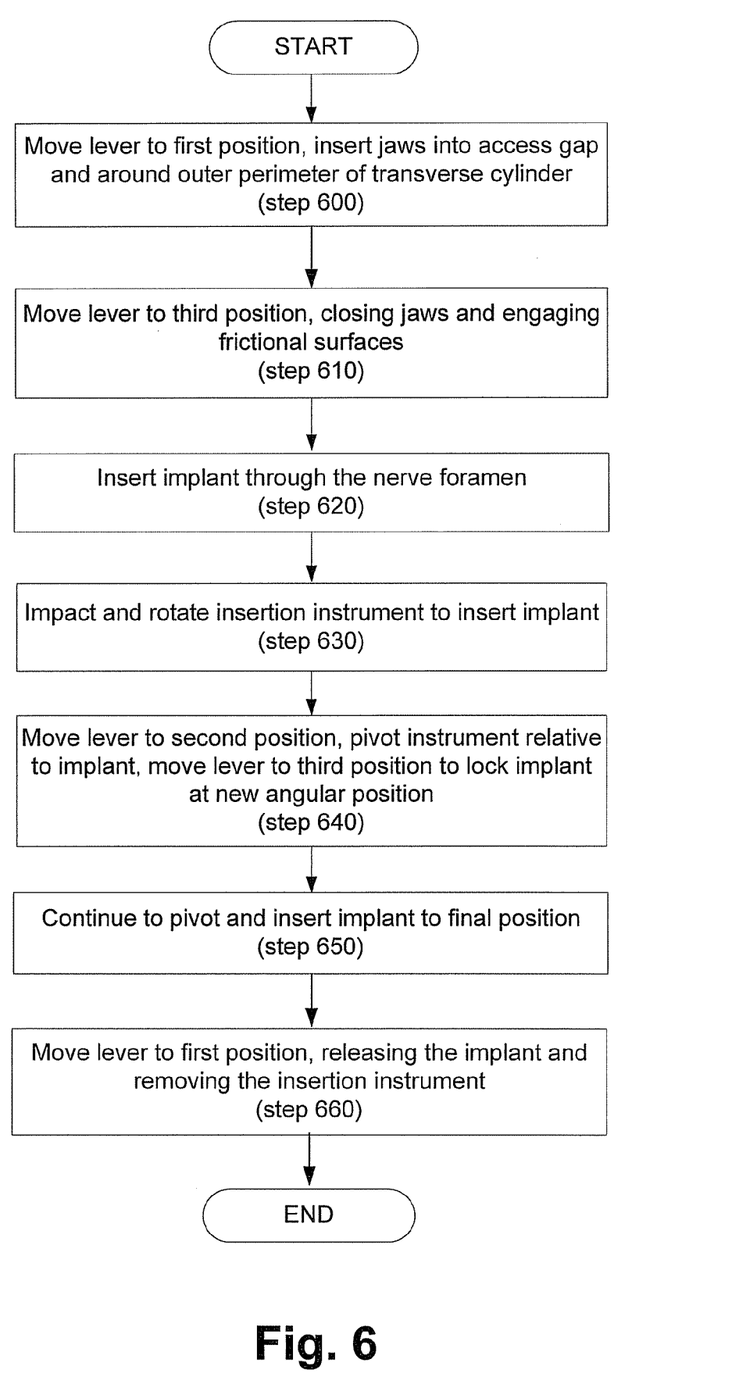
FIG. 6 is a flow chart illustrating a method of pivotably inserting an interbody spacer, according to one exemplary embodiment.

An exemplary method of inserting an interbody spacer using an insertion tool is described in FIG. 6 with reference to interaction between the interbody spacer as described in FIGS. 3A through 5B and the surgical process described in FIGS. 7 through 10. As illustrated in FIG. 6, the present exemplary method begins by the insertion instrument engaging the interbody spacer (step 600) as shown in FIGS. 3A and 3B. To initially engage the interbody spacer, the lever (220, FIG. 3A) is moved to the first position as shown in FIG. 3A. This opens the opposing jaws (240, 250; FIG. 3B). The jaws or jaw members (240, 250; FIG. 3B) are then inserted into the access gap (122, FIG. 2B) and around the outer perimeter of the transverse cylinder (116, FIG. 3B).

The spacer is then locked at the desired angle (step 610). Once the insertion instrument (200, FIG. 3A) is engaged with the interbody spacer (100, FIG. 3A) in the desired orientation, the lever (220, FIG. 3A) is moved to the third position as shown in FIGS. 5A-5B. This closes and retracts the jaws (240, 250; FIG. 5B), which pulls the spacer teeth (120, FIG. 5B) into contact with the shaft teeth (260), thereby restraining the interbody spacer (100) from pivoting with respect to the insertion instrument (200).

The insertion instrument with the attached interbody spacer (100) is then inserted into the surgical site (step 620). Now referring to FIG. 7, which illustrates the insertion of the interbody spacer (100) into the intervertebral space. The vertebra (700) comprises a vertebral body (750); a transverse process (730) connected to the vertebral body by a pedicle (770); a superior articular facet (720) connected to the spinous process (710) by a lamina (760). The spinal canal (740) passes between the pedicles (770) anterior to the lamina (760) and spinous process (710). A plurality of nerve foramen (not shown) provide space for nerves to exit the spinal column.

Figure 7:
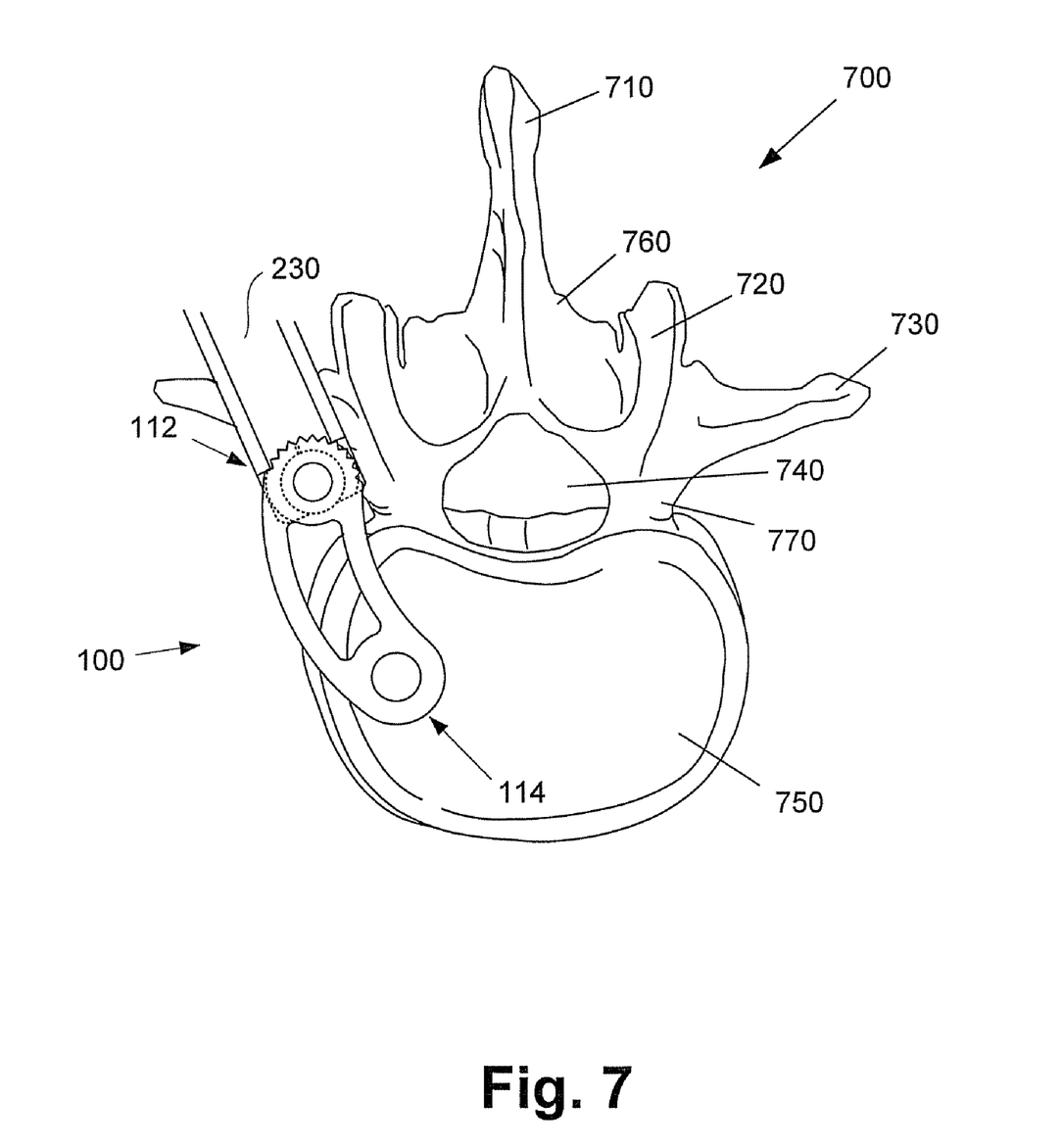
FIG. 7 is a side view of the pivotable interbody spacer being inserted using the method of FIG. 6, according to various exemplary embodiments.

In one exemplary embodiment, the interbody spacer is placed in the anterior space between adjoining vertebral bodies by the TLIF process. However, the present system and method may be used for any number of implant applications. As mentioned above, the TLIF process uses a posterior and lateral approach to access the disc space. To gain posterior and lateral access to the disc space, typically a facet joint is removed. The facet joint consists of a superior articular facet (720) and the inferior articular facet (not shown) of the adjoining vertebra. The required amount of bone removal is determined by the surgeon and varies from patient to patient. The removal of the facet joint allows access via the nerve foramen to the intervertebral space between the two vertebral bodies. After preparatory surgical procedures are performed, the interbody spacer (100) is inserted using the insertion instrument (200).

The spacer (100) enters the surgical site with the distal end (114) leading. As mentioned above, the distal end (114) has a double elliptical shape, which eases the insertion of the spacer into the surgical site.

Figure 8:
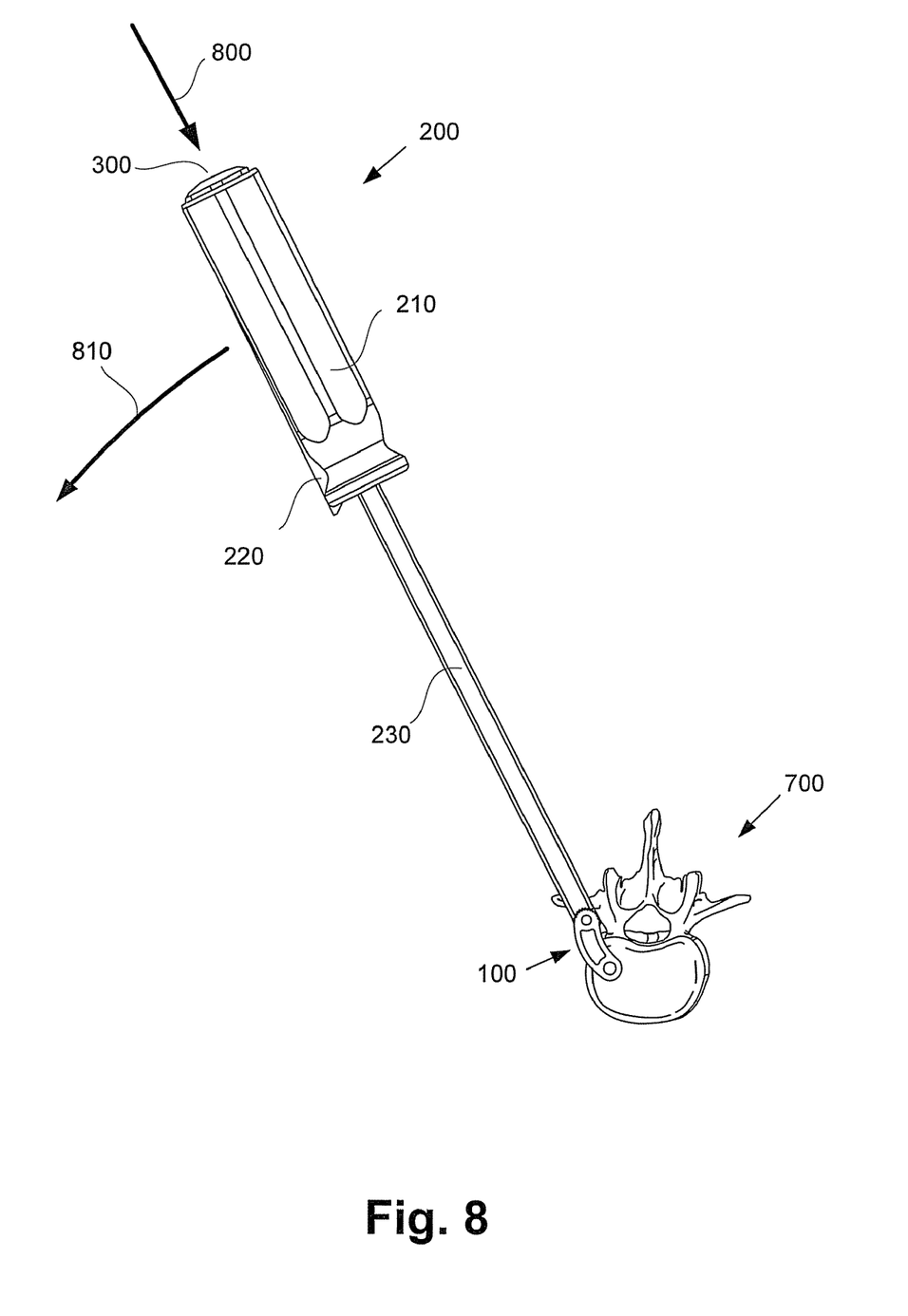
FIG. 8 is a side view of pivotably inserting an interbody spacer using the method of FIG. 6, according to various exemplary embodiments.

As shown in FIG. 8, the interbody spacer (100) may be inserted using a combination of simultaneous impaction and rotation (step 630, FIG. 6), followed by repositioning of the instrument about the implant. Impaction typically involves striking the impaction cap (300) on the end of handle, either manually or with another instrument as indicated by the straight arrow (800). The curved arrow (810) shows a rigid body rotation of the insertion instrument (200) and the fixably attached interbody spacer (100).

Once the spacer (100) can no longer be inserted in its coupled state, the instrument may be repositioned or pivoted relative to the spacer (100) to allow for further insertion and simultaneous rotation (step 640, FIG. 6). To pivot the insertion instrument (200) about the end of the spacer the lever is moved to the second position, which disengages the matching teeth (120, 260; FIG. 4) as shown in FIG. 4.

Figures 9A, 9B:
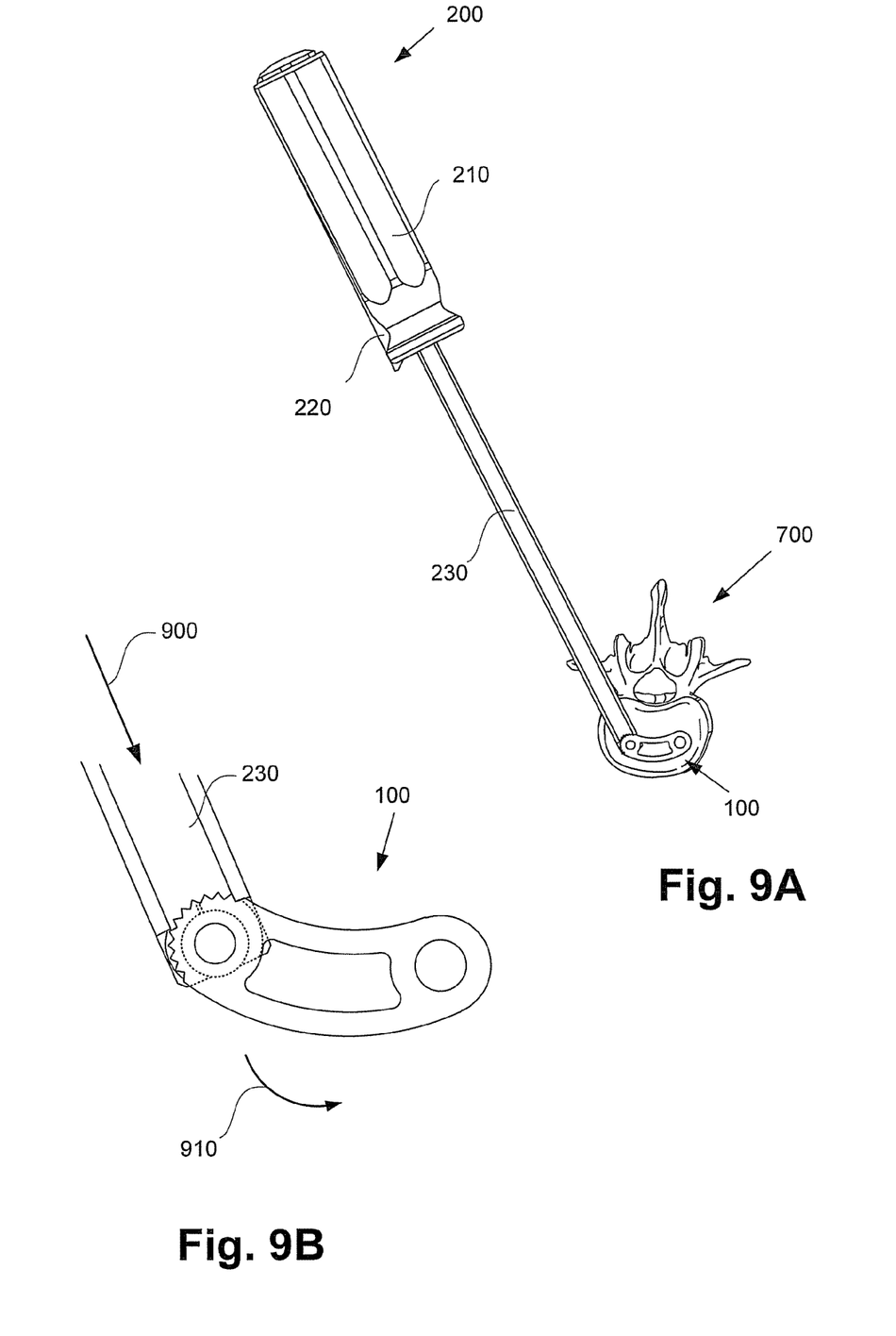
FIGS. 9A and 9B are side views of pivotably inserting an interbody spacer using the method of FIG. 6, according to various exemplary embodiments.

The insertion instrument can then be pivoted with respect to the partially inserted spacer (100) as shown in FIG. 9. The lever (220) is then returned to the third position. FIG. 9B shows the interbody spacer locked into a new angular position after the pivoting process. By pivoting the spacer (100), obstacles can be avoided and narrow or non-linear passageways can be followed without tamping the spacer into place. If required, the spacer can then be further inserted by impacting the insertion instrument as shown by the straight arrow (900) and by further rotation as shown by the curved arrow (910). The steps of pivoting and inserting the spacer are continued until the spacer is in its final position (step 650: FIG. 6).

Figure 10:
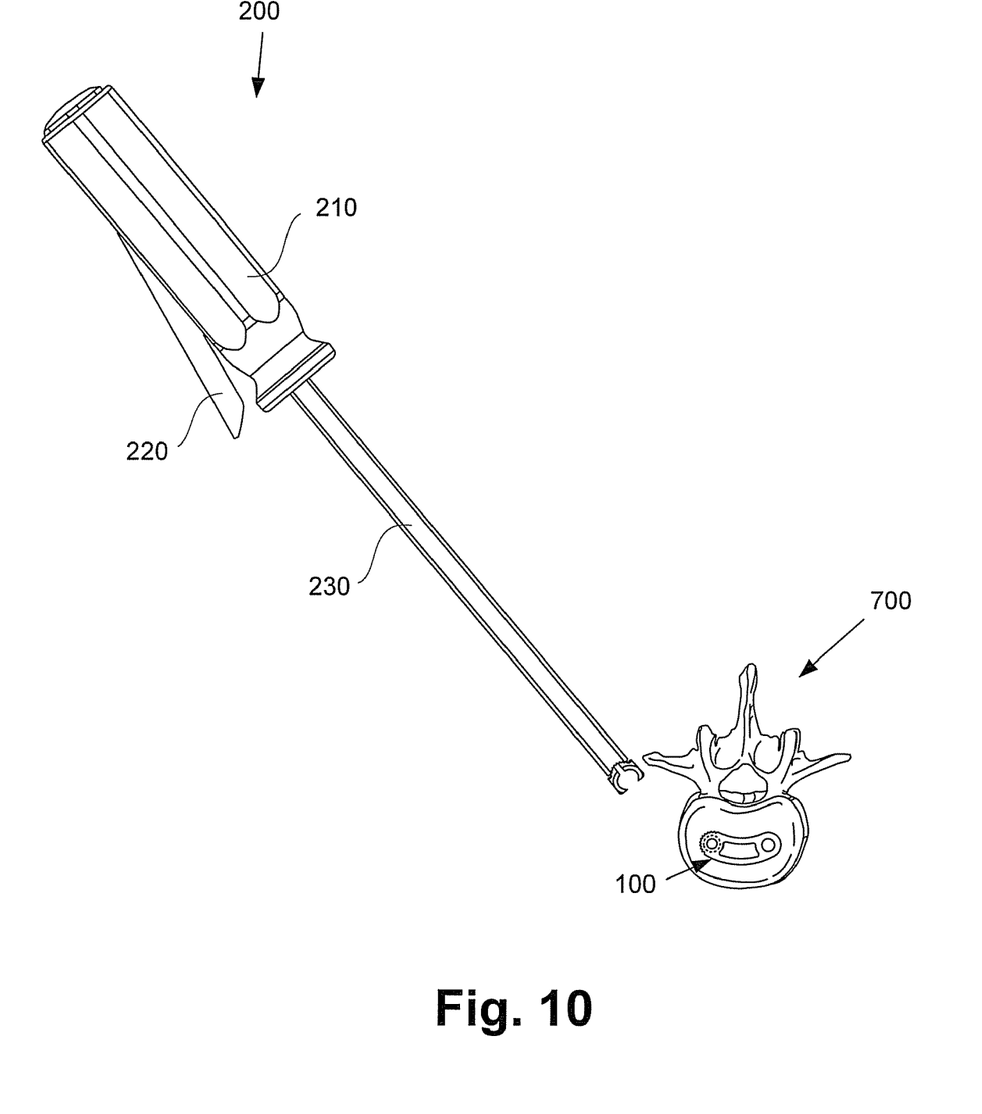
FIG. 10 is a side view of an interbody spacer in place and the insertion instrument being disengaged and withdrawn, according to various exemplary embodiments.

FIG. 10 illustrates the releasing of the spacer and the removal of the insertion instrument (step 660: FIG. 6). Once in a final position, the interbody spacer (100) is released from the insertion instrument (200) by moving the lever to the first position as illustrated in FIG. 10. The jaws or jaw members (240, 250) open and can then be disengaged from around the outer perimeter of the transverse cylinder (116, FIG. 1). The insertion instrument (200) is removed from the patient, leaving the interbody spacer correctly positioned within the surgical site.

In conclusion, the present exemplary systems and methods provide for a pivotable interbody spacer that provides a user with the ability to insert the spacer in a non-linear path. The insertion instrument can lock onto the interbody spacer at multiple angles to allow for the spacer to be pivoted in increments if the instrument rotation is restricted such that the instrument can only be rotated less than the total rotation required to position the spacer. This additional surgical flexibility can allow insertion of the interbody spacer with the removal of less tissue and bone which results in less invasive surgery, fewer post operative complications, and quicker patient recovery time.

Additionally, the present exemplary interbody spacer (100) employs geometry that provides for a small spacer with relatively large surface area and internal cavity. The spacer is hollowed out to increase cavity volume and surface area while minimizing overall size. Additionally the present exemplary systems and methods allow for rotation of the spacer for final positioning without having to release the spacer and tamp the spacer into place. Because the insertion instrument is not required to be disengaged from the spacer, quicker and simpler surgeries are possible.

The preceding description has been presented only to illustrate and describe the present methods and systems. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What we claim is:

1. A method for inserting an interbody spacer into a surgical site comprising:
   creating a coupled connection between said interbody spacer and an insertion instrument such that said interbody spacer is free to rotate with respect to said insertion instrument about at least one degree of freedom, said coupled connection comprises a plurality of movable jaws extending from said insertion instrument, moving said jaws with respect to each other and enclosing a portion of said interbody spacer within said plurality of jaws;
   fixing said interbody spacer in a first angular orientation with respect to said insertion instrument;
   inserting said interbody spacer into said surgical site;
   releasing said interbody spacer from said first angular position while maintaining said coupled connection;
   pivoting said insertion instrument about said coupled connection such that said interbody spacer is in a second angular position with respect to said insertion instrument;
   fixing said interbody spacer in said second angular position; and
   further inserting and rotating said interbody spacer.

2. The method of claim 1 wherein said interbody spacer is fixed in an angular position by selectively engaging a frictional feature on said interbody spacer with a portion of said insertion instrument.

3. The method of claim 2 wherein said frictional feature on said interbody spacer is a first plurality of teeth.

4. The method of claim 3 wherein said first plurality of teeth is disposed about an outer surface of said spacer.

5. The method of claim 4 wherein said angular position is fixed by selectively engaging said first plurality of teeth on said interbody spacer with a second plurality of teeth disposed on said insertion instrument.

6. The method of claim 5 wherein said first plurality of teeth and said second plurality of teeth are engaged by retracting said jaws into said insertion instrument.

7. A method for inserting an interbody spacer into a surgical site comprising:
   creating a posterior lateral opening into a disc space;
   providing a spacer for insertion into said disc space;
   rotatably coupling said spacer to an instrument in a first position by inserting a post member of said spacer between a plurality of expanded jaws;
   moving said plurality of expanding jaws with respect to each other;
   merging said plurality of expanded jaws together and retaining said post member between said plurality of expanding jaws;
   positioning a leading end of said spacer at said opening;
   fully engaging said spacer with said instrument in a second position, wherein said second position prevents rotation of said spacer;

simultaneously impacting and rotating spacer into said spinal disc space;

placing said instrument in said first position; and re-orienting said instrument relative to said spacer in preparation for further impaction and rotation.

8. The method of claim 7, wherein said insertion is performed through a tube.

9. The method of claim 7, wherein said fully engaging said spacer with said instrument in a second position comprises retracting said plurality of expanding jaws to engage said spacer with at least one retention member formed on said instrument.

10. The method of claim 9, wherein said re-orienting said instrument relative to said spacer in preparation for further impaction and rotation comprises rotating said spacer relative to said at least one retention member formed on said instrument.

11. A spinal spacer manipulation device, comprising:

a handle member;

an extension member including a first and a second end, wherein said first end of said extension member is coupled to said handle member;

a means for selectively coupling a spacer to said second end of said extension member, said means for selectively coupling comprises a plurality of retractably jaw members protruding from said second end of said extension member;

said plurality of retractably jaw members being movable with respect to each other;

a means for selectively extending said retractably jaw members away from said second end of said extension member and selectively withdrawing said retractably jaw members back toward said second end of said extension member;

a means for selectively fixing said spacer in an angular position with respect to said spinal spacer manipulation device;

a means for actuating said means for selectively coupling and said means for selectively fixing.

12. The device of claim 11 wherein said means for actuating comprises actuation member coupled to said retractable jaw members, wherein said actuation member is configured to selectively merge and retract said jaw members.

13. The spinal spacer manipulation device of claim 12, wherein said actuation member is configured to be positioned in a first, a second, and third actuation position, wherein said first actuation position disposes said retractable jaw members in a separated and extended position;

wherein said second actuation position disposes said retractable jaw members in a merged and extended position; and wherein said third actuation position disposes said retractable jaw members in a merged and retracted position.

14. The spinal spacer manipulation device of claim 13, wherein said actuation member is disposed on said handle member.

15. The spinal spacer manipulation device of claim 14, wherein said means for selectively fixing said spacer in an angular position comprises at least one engagement member formed on said second end of said extension member.

16. The spinal spacer manipulation device of claim 15, wherein said at least one engagement member comprises at least one protrusion configured to frictionally engage a surface of said spinal spacer.

* * * * *